United States Patent
Seo

(10) Patent No.: US 8,820,048 B2
(45) Date of Patent: Sep. 2, 2014

(54) SYSTEM AND METHOD FOR DETECTING POLLUTION BY POISONOUS MATERIAL FOR AIR EXHAUSTER OF VEHICLE

(75) Inventor: Jung Min Seo, Suwon-si (KR)

(73) Assignees: Hyundai Motor Company, Seoul (KR); Kia Motors Corp., Seoul (KR)

(*) Notice: Subject to any disclaimer, the term of this patent is extended or adjusted under 35 U.S.C. 154(b) by 456 days.

(21) Appl. No.: 13/316,550

(22) Filed: Dec. 11, 2011

(65) Prior Publication Data
US 2013/0067989 A1 Mar. 21, 2013

(30) Foreign Application Priority Data
Sep. 21, 2011 (KR) ........................ 10-2011-0095038

(51) Int. Cl.
| | | |
|---|---|---|
| F01N 11/00 | (2006.01) | |
| G01M 15/10 | (2006.01) | |
| G01N 25/28 | (2006.01) | |
| F02D 41/14 | (2006.01) | |
| F02D 41/02 | (2006.01) | |
| F01N 9/00 | (2006.01) | |

(52) U.S. Cl.
CPC .............. *F02D 41/027* (2013.01); *Y02T 10/47* (2013.01); *G01N 25/28* (2013.01); *F02D 41/1446* (2013.01); *F01N 2550/02* (2013.01); *F01N 2560/06* (2013.01); *F01N 11/002* (2013.01); *F02D 41/1447* (2013.01); *F02D 41/1444* (2013.01); *F01N 2900/1404* (2013.01); *F01N 9/007* (2013.01)
USPC .............................. 60/277; 60/274; 73/114.77

(58) Field of Classification Search
CPC . F01N 9/007; F01N 2550/00; F01N 2550/02; F01N 2550/20; F01N 2560/06; F01N 2900/1404; Y02T 10/47; F01D 41/1445; F01D 41/1446; F01D 41/1447
USPC ...................... 73/114.75, 114.77; 60/274, 277
See application file for complete search history.

(56) References Cited

U.S. PATENT DOCUMENTS

| | | | | | |
|---|---|---|---|---|---|
| 5,170,147 | A | * | 12/1992 | Graffagno et al. ............. | 340/449 |
| 5,592,815 | A | * | 1/1997 | Jelden et al. ..................... | 60/274 |
| 5,675,967 | A | * | 10/1997 | Ries-Mueller .................. | 60/274 |
| 5,722,238 | A | * | 3/1998 | Tanahashi et al. .............. | 60/276 |
| 5,740,675 | A | * | 4/1998 | Shimasaki et al. .............. | 60/274 |

(Continued)

FOREIGN PATENT DOCUMENTS

| | | |
|---|---|---|
| JP | 2004-300981 | 10/2004 |
| JP | 2010-185448 | 8/2010 |

*Primary Examiner* — Lisa Caputo
*Assistant Examiner* — Punam Roy
(74) *Attorney, Agent, or Firm* — Morgan, Lewis & Bockius LLP

(57) ABSTRACT

A system for detecting pollution by a poisonous material for an air exhauster of a vehicle may include a temperature sensor provided to the flow line of an exhaust gas and having a catalyst material that causes an exothermic reaction with a pollution material in the exhaust gas, and a controller which stores a standard temperature value of the temperature sensor and operates in such a manner that the exhaust gas may be heated under control of an engine control unit when the temperature value drops by a predetermined amount from the standard temperature value, and that the catalyst material may be determined to have deteriorated when a measured temperature value after heating may be less than the standard temperature value, so that the standard temperature value may be replaced with the measured temperature value, and to a detection method using the same.

9 Claims, 2 Drawing Sheets

(56) References Cited

U.S. PATENT DOCUMENTS

| | | | |
|---|---|---|---|
| 5,851,376 A * | 12/1998 | Nishioka et al. | 205/784.5 |
| 5,922,287 A * | 7/1999 | Kato et al. | 422/95 |
| 6,258,232 B1 * | 7/2001 | Hasegawa et al. | 204/424 |
| 6,482,650 B1 * | 11/2002 | Kato et al. | 436/37 |
| 6,506,605 B1 * | 1/2003 | Allen et al. | 436/37 |
| 6,571,602 B2 * | 6/2003 | Ohkuma | 73/23.32 |
| 6,797,517 B1 * | 9/2004 | Hoshi et al. | 436/37 |
| 7,286,926 B2 * | 10/2007 | Gotoh et al. | 701/114 |
| 7,297,240 B2 * | 11/2007 | Hattori | 204/401 |
| 7,409,821 B2 * | 8/2008 | Miura | 60/277 |
| 7,418,322 B2 * | 8/2008 | Kariya et al. | 701/30.2 |
| 7,523,653 B2 * | 4/2009 | Smith et al. | 73/114.69 |
| 7,670,047 B2 * | 3/2010 | Okayasu et al. | 374/57 |
| 7,707,821 B1 * | 5/2010 | Legare | 60/277 |
| 7,797,927 B2 * | 9/2010 | Nagaoka et al. | 60/277 |
| 8,079,351 B2 * | 12/2011 | Uhrich et al. | 123/688 |
| 8,091,415 B2 * | 1/2012 | Matsunaga et al. | 73/114.69 |
| 8,105,561 B2 * | 1/2012 | Hatanaka et al. | 423/213.5 |
| 8,303,174 B2 * | 11/2012 | Kasahara | 374/144 |
| 8,490,385 B2 * | 7/2013 | Miyoshi et al. | 60/277 |
| 2003/0097873 A1 * | 5/2003 | Surnilla | 73/118.1 |
| 2005/0102076 A1 * | 5/2005 | Kariya et al. | 701/34 |
| 2008/0083271 A1 * | 4/2008 | He et al. | 73/118.1 |
| 2008/0295489 A1 * | 12/2008 | Elfvik | 60/277 |
| 2009/0090097 A1 * | 4/2009 | Gaskins | 60/277 |
| 2010/0319316 A1 * | 12/2010 | Kasahara | 60/273 |
| 2011/0271659 A1 * | 11/2011 | Umemoto et al. | 60/276 |
| 2012/0023913 A1 * | 2/2012 | Yoshioka et al. | 60/285 |
| 2013/0008149 A1 * | 1/2013 | Ukropec et al. | 60/274 |
| 2013/0255228 A1 * | 10/2013 | SAKAMOTO et al. | 60/274 |

* cited by examiner

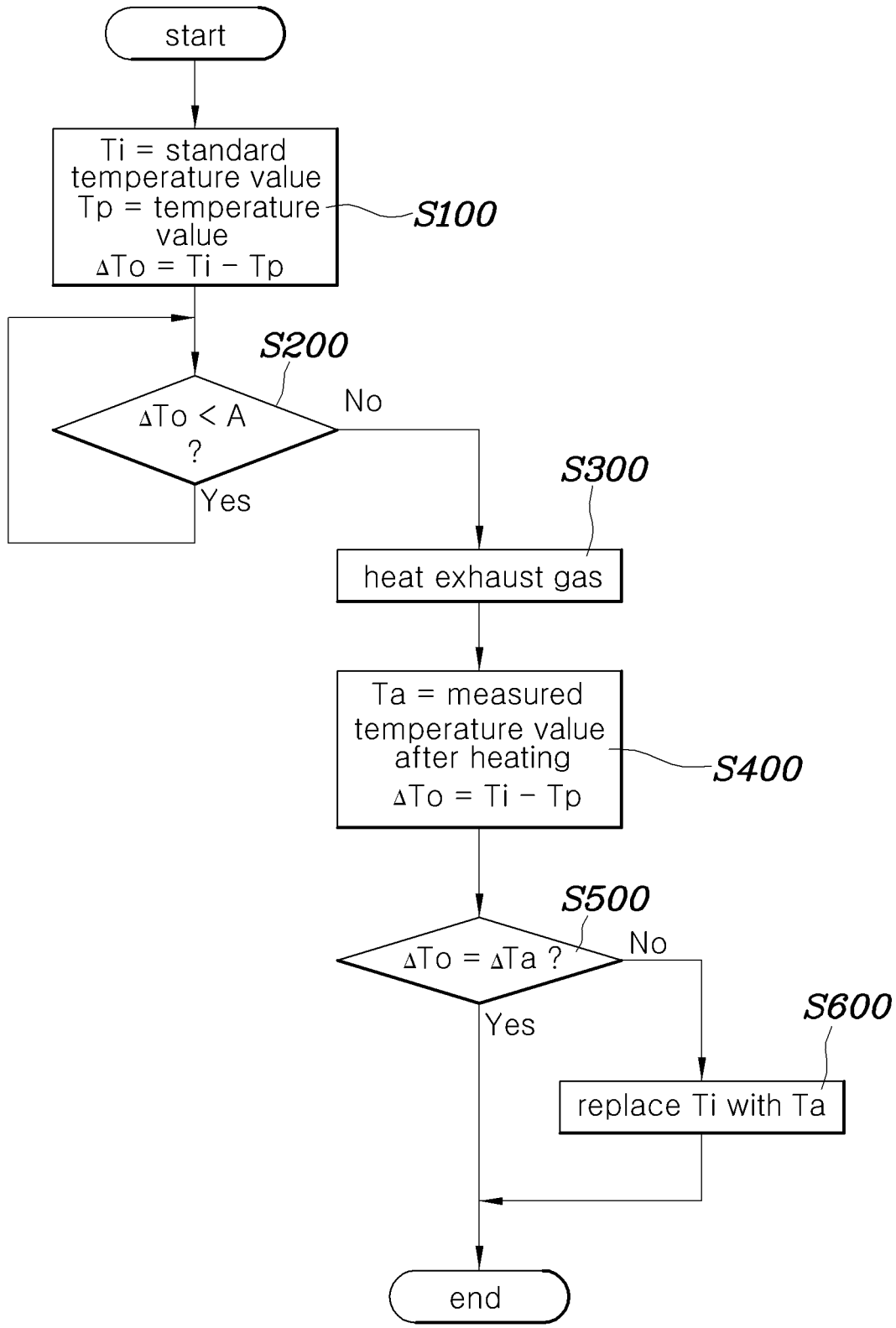

SYSTEM AND METHOD FOR DETECTING POLLUTION BY POISONOUS MATERIAL FOR AIR EXHAUSTER OF VEHICLE

CROSS-REFERENCE TO RELATED APPLICATION

The present application claims priority to Korean Patent Application No. 10-2011-0095038, filed on Sep. 21, 2011, the entire contents of which is incorporated herein for all purposes by this reference.

BACKGROUND OF THE INVENTION

1. Field of the Invention

The present invention relates to a system and method for detecting pollution by a poisonous material for an air exhauster of a vehicle, which automatically minimizes the degradation of the function of a catalyst device that is responsible for exhaust purification while combusting and discharging a sulfur component contained in an exhaust gas upon driving of a vehicle.

2. Description of Related Art

Conventionally in order to achieve effects of the present invention regarding a system and method for detecting pollution by a poisonous material in an air exhauster of a vehicle which automatically minimizes the degradation of the function of a catalyst device responsible for exhaust purification while combusting and discharging a sulfur component contained in an exhaust gas upon driving of a vehicle, techniques for detecting the poisoning of a catalyst by mounting a temperature sensor upstream of the catalyst of an exhaust system and monitoring a difference in heat value before and after poisoning of the catalyst have been introduced.

Further, a signal in response to such detection is transmitted to an engine control unit (ECU), so that conditions of the exhaust gas are controlled to eliminate the poison from the catalyst, thereby restoring the function of the catalyst.

Specifically in conventional techniques, a catalyst or an adsorbent, which causes an exothermic reaction with a reaction material contained in gas, is applied onto the surface of the temperature sensor.

When the catalyst or adsorbent causes an exothermic reaction with the reaction material of the gas on the temperature sensor, the temperature elevated by the exothermic reaction is detected by means of the temperature sensor. Then, the catalyst or adsorbent poisoned by sulfur comes into contact with the exhaust gas, thus lowering the heat temperature, and such a difference in temperature is quantified to detect the state of pollution caused by the sulfur, after which a sufficient fuel condition is embodied in an engine and the occluded poisonous material is thereby detached.

However, these methods are problematic because the degradation of the heating function of the temperature sensor is more greatly affected by the lowered heat value due to thermal deterioration of the catalyst or occluding material applied on the surface of the sensor, than by the pollution by the poisonous material, undesirably making it difficult to actually detect only pollution by the poisonous material.

Therefore, techniques are required that use a temperature sensor and a catalyst, in which deterioration factors are removed and only the actual factors that result in a decrease in heat that come from pollution by a poisonous material are discovered so as to accurately detect the pollution.

This related art is merely utilized to enhance understanding about the background of the present invention, and should not be regarded as conventional techniques known to those having ordinary knowledge in the art.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing a system and method for detecting pollution by a poisonous material for an air exhauster of a vehicle, in which the function of a catalyst is maximally retained even without performing any additional operation thus reducing the discharge of gas and improving the environmentally friendly image of vehicles.

In an aspect of the present invention, a system for detecting pollution by a poisonous material for an air exhauster of a vehicle, may include a temperature sensor provided to a flow line of an exhaust gas and having a catalyst material that causes an exothermic reaction with a pollution material in the exhaust gas, and a controller which stores a standard temperature value (Ti) of the temperature sensor and operates in such a manner that the exhaust gas is heated under control of an engine control unit when a temperature value drops by a predetermined amount from the standard temperature value (Ti), and that the catalyst material is determined to may have deteriorated when a measured temperature value (Ta) after heating is less than the standard temperature value (Ti) or when a difference between the measured temperature value (Ta) and a peak temperature value (Tp) determined when S components accumulate on a catalyst of the temperature sensor is not equal to a difference between the standard temperature value (Ti) and the peak temperature value (Tp), so that the standard temperature value (Ti) is replaced with the measured temperature value (Ta).

The pollution material is a sulfur (S) component, and the catalyst material is a palladium (Pd) component or a platinum (Pt) component.

The standard temperature value is a temperature measurement value of the temperature sensor measured in an initial exhaust gas.

The controller performs at least two measurements to obtain measured temperature values and compares an average value of the measured temperature values with the standard temperature value.

The controller sends a warning signal when a temporal cycle for requesting heating of the exhaust gas by the engine control unit is shortened within a predetermined time period.

In another aspect of the present invention, a method of detecting pollution by a poisonous material for an air exhauster of a vehicle, may include measuring and storing a standard temperature value of a temperature sensor provided to a flow line of an exhaust gas and having a catalyst material that causes an exothermic reaction with a pollution material (S100), heating the exhaust gas under control of an engine control unit when a temperature value of the temperature sensor drops by a predetermined amount from the standard temperature value (S300), and determining the catalyst material to may have deteriorated when a measured temperature value (Ta) after heating of the exhaust gas is less than the standard temperature value (Ti) or when a difference between the measured temperature value (Ta) and a peak temperature value (Tp) determined when S components accumulate on a catalyst of the temperature sensor is not equal to a difference between the standard temperature value (Ti) and the peak temperature value (Tp), so that the standard temperature value (Ti) is replaced with the measured temperature value (Ta) (S600).

The standard temperature value is a temperature measurement value of the temperature sensor measured in an initial exhaust gas.

At least two measurements are performed to obtain measured temperature values and an average value of the measured temperature values is compared with the standard temperature value.

The method may include giving a driver a warning when a temporal cycle for requesting heating of the exhaust gas by the engine control unit is shortened within a predetermined time period.

The methods and apparatuses of the present invention have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

FIG. 3 is a flowchart showing a detection process using the system for detecting pollution by a poisonous material for an air exhauster of a vehicle shown in FIG. 1.

Figure 1:
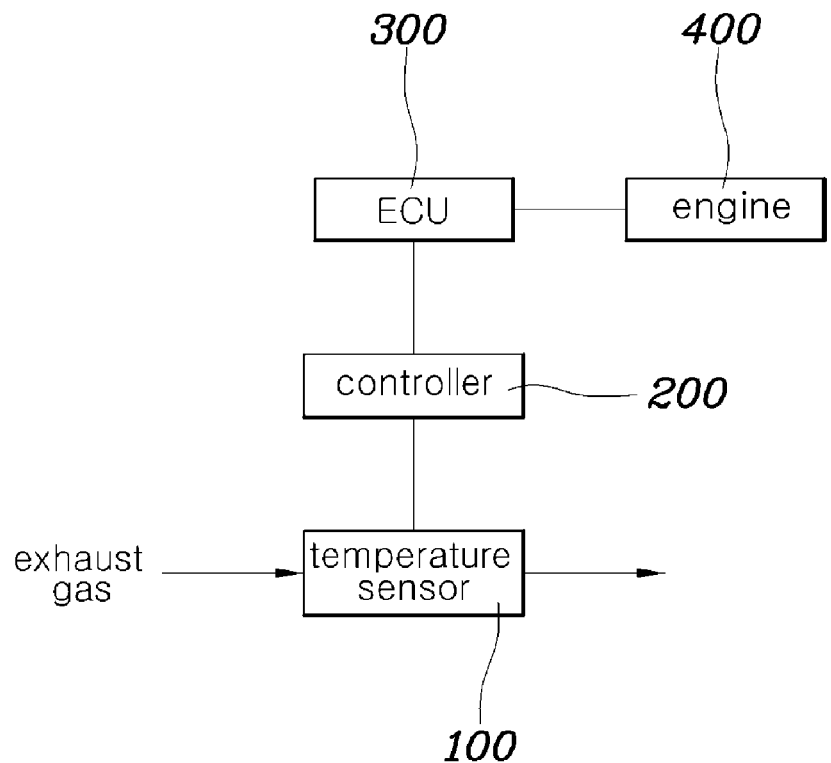
FIG. 1 is a block diagram showing a system for detecting pollution by a poisonous material for an air exhauster of a vehicle, according to an exemplary embodiment of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Hereinafter, a system and method for detecting pollution by a poisonous material for an air exhauster of a vehicle according to exemplary embodiments of the present invention will be described with reference to the accompanying drawings.

Figure 2:
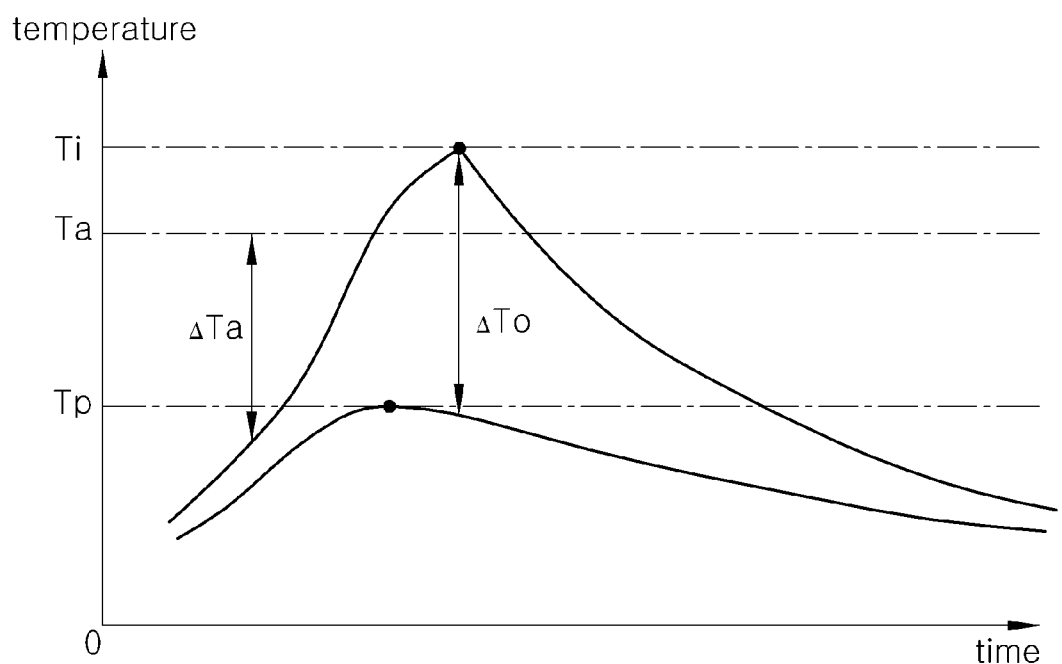
FIG. 2 is a graph showing the temperature of an exhaust gas in order to explain the system for detecting pollution by a poisonous material for an air exhauster of a vehicle shown in FIG. 1.

FIG. 1 shows a system for detecting pollution by a poisonous material for an air exhauster of a vehicle according to an exemplary embodiment of the present invention, and FIG. 2 is a graph showing the temperature of an exhaust gas in order to explain the system for detecting pollution by a poisonous material for an air exhauster of a vehicle of FIG. 1.

The system for detecting pollution by a poisonous material for an air exhauster of a vehicle according to an exemplary embodiment of the present invention includes a temperature sensor 100 provided to the flow line of an exhaust gas and having a catalyst material that causes an exothermic reaction with a pollution material in the exhaust gas, and a controller 200 which stores a standard temperature value of the temperature sensor 100 and operates in such a manner that the exhaust gas is heated under control of an ECU 300 when the temperature value drops by a predetermined amount from the standard temperature value, and that the catalyst material is determined to have deteriorated when a measured temperature value after heating is less than the standard temperature value, so that the standard temperature value is replaced with the measured temperature value.

The air exhauster of a vehicle may be variously configured, and specific examples thereof are as follows.

DOC (Diesel Oxidation Catalyst) only
DOC+DPF (Diesel Particulate Filter)
(DOC)+LNT (Lean Nox Trap)+DPF
DOC+DPF+SCR (Selective Catalytic Reduction)
DOC+SCR+DPF
TWC (Three Way Catalytic converter)+DOC+LNT+DPF+SCR
DOC+DPF+LNT The above air exhauster has been already known and a detailed description thereof will be omitted. The temperature sensor according to an exemplary embodiment of the present invention is mounted upstream or downstream of the air exhauster thus configured, to measure heat of the catalyst applied on the temperature sensor.

For example, assume that the pollution material is a sulfur (S) component, and that the catalyst material is a palladium (Pd) component or a platinum (Pt) component. In the case of an S component, a Pd or Pt catalyst causes an exothermic reaction that releases heat via oxidation. Specifically, when an exhaust gas is generated, the S component contained in the exhaust gas reacts with the Pd of the temperature sensor to generate heat, followed by measuring such heat, after which whether the air exhauster is being desulfurized is determined by the controller. If desulfurization is required, the temperature of the exhaust gas may be elevated by means of the ECU, so that the S component is separated from the catalyst.

To make such an operation accurate, the controller stores the standard temperature value of the temperature sensor 100, and the exhaust gas is heated under control of the ECU 300 when the temperature value drops by a predetermined amount from the standard temperature value, and the catalyst material is determined to have deteriorated when the measured temperature value after heating is less than the standard temperature value, so that the standard temperature value is replaced with the measured temperature value.

As shown in FIG. 2, the temperature value of the temperature sensor has a trend of increasing in proportion to an increase in the amount of generated exhaust gas because of the exothermic reaction between S and catalyst, and then of gradually decreasing again due to a decrease in the reaction while attaching the S component to the catalyst. The peak in such a temperature range is set to the temperature value and compared, whereby the point of time of desulfurization may be determined.

In FIG. 2, Ti is a peak temperature value in an initial state, and the standard temperature value is the temperature measurement value of the temperature sensor measured in an initial exhaust gas, namely means an initial value when the catalyst is a not-yet deteriorated state.

In the case where the S component accumulates on the catalyst of the temperature sensor, the temperature decreases and consequently the peak is shown as Tp. Thus the case where Tp is lower by at least a predetermined amount than Ti may be used as the point in time at which the air exhauster itself requires desulfurization.

Accordingly, the controller increases the temperature of the exhaust gas under control of the ECU, and the S component is removed again from the catalyst by means of the hot exhaust gas, whereby the catalyst is automatically regenerated so as to be able to exhibit its normal functions.

However, in the case where the catalyst material is exposed to high temperature for a long period of time, it may create lumps due to self-deterioration, and thus the surface area of the catalyst is reduced making it difficult to manifest its original performance.

Hence, there is a need to adjust the standard point Ti. Specifically, despite the catalyst normally regenerating after the exhaust gas has been heated, the peak temperature value is typically represented by Ta. Thus $\Delta T0$ corresponding to a difference between Ti and Tp is compared with $\Delta Ta$ which is a difference between Ta and Tp, and thereby whether a decrease in the heat of the catalyst is based on either poisoning or self-deterioration is determined.

Accordingly, the controller 200 operates in such a manner that the catalyst material is determined to have deteriorated when the measured temperature value (Ta) after heating is less than the standard temperature value (Ti), so that the standard temperature value (Ti) is replaced with the measured temperature value (Ta).

Specifically, in the case where $\Delta Ta$ is less than $\Delta T0$, Ti is replaced with Ta, so that poisoning and deterioration are differentiated from each other. Otherwise, in a case where the initial Ti is continuously fixed, the temperature value is always determined to be insufficient, and the temperature of the exhaust gas is maintained high for an excessively long period of time. In that case, deterioration of the catalyst due to the high temperature may continue, undesirably shortening the life of the catalyst.

The present invention is intended to solve such problems, and the function of the catalyst is maximally retained even without the need to perform any additional operation, thus reducing the discharge of gas and improving the environmentally friendly image of a vehicle.

Furthermore, the generation of white smoke may be controlled not only upon removal of SOx from a NOx trap catalyst but also upon desulfurization and regeneration of DPF in an air exhauster under high S conditions.

Specifically, by solving conventional problems that result from not taking into consideration the difference in heat value because of thermal deterioration, the ability to detect sulfur pollution may be enhanced, and a warning is given to a consumer when fuel oil is supplied in a base value or more, and thus the rate of deterioration of a vehicle is retarded. Furthermore, the pollution is excluded by periodic desulfurization according to EU4 exhaust emission standards using only diesel oxidation catalysts, thus reducing the consumption of precious metal.

Also in the controller 200, measured temperature values are obtained via at least two measurements and the average value thereof is compared with the standard temperature value, thus increasing the accuracy of measurement.

Moreover, when the temporal cycle for requesting the heating of the exhaust gas using the ECU 300 is shortened within a predetermined time period, the controller 200 sends a warning signal thus letting a driver know that the fuel is in a state of containing a large amount of S component, so that high reliability of the system is provided to a driver and inferior fuel can be discovered. Thereby, the environment may be protected and the durability life of the catalyst may increase.

FIG. 3 is a flowchart showing the detection process using the system for detecting pollution by a poisonous material for an air exhauster of a vehicle shown in FIG. 1. The method of detecting pollution by a poisonous material for an air exhauster of a vehicle according to an exemplary embodiment of the present invention includes measuring and storing a standard temperature value of a temperature sensor provided to the flow line of an exhaust gas and having a catalyst material that causes an exothermic reaction with a pollution material (S100), heating the exhaust gas under control of an ECU when the temperature value of the temperature sensor drops by a predetermined amount from the standard temperature value (S300), and determining that the catalyst material has deteriorated when a measured temperature value after heating of the exhaust gas is less than the standard temperature value, so that the standard temperature value is replaced with the measured temperature value (S600).

Specifically, the initial standard temperature value is set to Ti and the peak of the subsequently measured temperature range is designated to Tp, and the difference between Ti and Tp is designated to $\Delta T0$ (S100).

Then, when the $\Delta T0$ is less than A, namely, when the catalyst does not generate heat, the catalyst is determined to have been poisoned, and the exhaust gas is heated (S200, S300). Accordingly, the sulfur component will again be separated from the poisoned catalyst.

The peak of the temperature range measured again after heating is designated to Ta, and $\Delta Ta$ is designated to a difference between Ta and Tp (S400). Then, $\Delta Ta$ is compared with $\Delta T0$. If $\Delta Ta$ is less than $\Delta T0$, the catalyst is determined to have deteriorated, and Ti is replaced with Ta.

Thereby, the deteriorated state is differentiated from the poisoned state, and thus unnecessary heating of the exhaust gas is prevented thereby solving the problems of the deterioration of the catalyst.

In S600, at least two measurements are performed thus obtaining measured temperature values, and the average value thereof is compared with the standard temperature value. Also, the detection method according to an exemplary embodiment of the present invention may further include giving a driver a warning when the temporal cycle for requesting the heating of the exhaust gas by the ECU is shortened within a predetermined time period.

As described hereinbefore, the present invention provides a system and method for detecting pollution by a poisonous material for an air exhauster of a vehicle. According to an exemplary embodiment of the present invention, the function of a catalyst can be maximally retained even without the need to perform any additional operation, thus reducing the discharge of gas, and improving an environmentally friendly image of a vehicle.

Also according to an exemplary embodiment of the present invention, the generation of white smoke can be controlled not only upon removal of SOx from a NOx trap catalyst but also upon desulfurization and regeneration of DPF in an air exhauster under high S conditions.

Specifically, conventional problems that result from not taking the difference in heat value due to thermal deterioration into consideration are solved, whereby the ability to detect sulfur pollution can be enhanced, and a warning can be given to a consumer when fuel oil is supplied in a base value or more, so that the rate of deterioration of a vehicle is retarded. Furthermore, the pollution is excluded by periodic desulfurization according to EU4 exhaust emission standards using only diesel oxidation catalysts, thus reducing the consumption of precious metal.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A system for detecting pollution by a poisonous material for an air exhauster of a vehicle, comprising:
    a temperature sensor provided to a flow line of an exhaust gas and having a catalyst material that causes an exothermic reaction with a pollution material in the exhaust gas; and
    a controller which stores a standard temperature value (Ti) of the temperature sensor and operates in such a manner that the exhaust gas is heated under control of an engine control unit when a temperature value drops by a predetermined amount from the standard temperature value (Ti), and that the catalyst material is determined to have deteriorated when a measured temperature value (Ta) after heating is less than the standard temperature value (Ti) or when a difference between the measured temperature value (Ta) and a peak temperature value (Tp) determined when S components accumulate on a catalyst of the temperature sensor is not equal to a difference between the standard temperature value (Ti) and the peak temperature value (Tp), so that the standard temperature value (Ti) is replaced with the measured temperature value (Ta).

2. The system of claim 1, wherein the pollution material is a sulfur (S) component, and the catalyst material is a palladium (Pd) component or a platinum (Pt) component.

3. The system of claim 1, wherein the standard temperature value is a temperature measurement value of the temperature sensor measured in an initial exhaust gas.

4. The system of claim 1, wherein the controller performs at least two measurements to obtain measured temperature values and compares an average value of the measured temperature values with the standard temperature value.

5. The system of claim 1, wherein the controller sends a warning signal when a temporal cycle for requesting heating of the exhaust gas by the engine control unit is shortened within a predetermined time period.

6. A method of detecting pollution by a poisonous material for an air exhauster of a vehicle, comprising:
    measuring and storing a standard temperature value of a temperature sensor provided to a flow line of an exhaust gas and having a catalyst material that causes an exothermic reaction with a pollution material (S100);
    heating the exhaust gas under control of an engine control unit when a temperature value of the temperature sensor drops by a predetermined amount from the standard temperature value (S300); and
    determining the catalyst material to have deteriorated when a measured temperature value (Ta) after heating of the exhaust gas is less than the standard temperature value (Ti) or when a difference between the measured temperature value (Ta) and a peak temperature value (Tp) determined when S components accumulate on a catalyst of the temperature sensor is not equal to a difference between the standard temperature value (Ti) and the peak temperature value (Tp), so that the standard temperature value (Ti) is replaced with the measured temperature value (Ta) (S600).

7. The method of claim 6, wherein, in S100, the standard temperature value is a temperature measurement value of the temperature sensor measured in an initial exhaust gas.

8. The method of claim 6, wherein, in S600, at least two measurements are performed to obtain measured temperature values and an average value of the measured temperature values is compared with the standard temperature value.

9. The method of claim 6, further comprising giving a driver a warning when a temporal cycle for requesting heating of the exhaust gas by the engine control unit is shortened within a predetermined time period.

* * * * *